United States Patent
Reiter et al.

(10) Patent No.: US 9,435,780 B2
(45) Date of Patent: Sep. 6, 2016

(54) METHOD AND DEVICE FOR TESTING BOX BLANKS

(71) Applicant: Texmag GmbH Vertriebsgesellschaft, Thalwil (CH)

(72) Inventors: Thomas Reiter, Odelzhausen (DE); Lars Zwerger, Augsburg (DE)

(73) Assignee: TEXMAG GMBH VERTRIEBSGESELLSCHAFT, Thalwil (CH)

(*) Notice: Subject to any disclaimer, the term of this patent is extended or adjusted under 35 U.S.C. 154(b) by 340 days.

(21) Appl. No.: 14/183,068

(22) Filed: Feb. 18, 2014

(65) Prior Publication Data

US 2014/0238134 A1    Aug. 28, 2014

(30) Foreign Application Priority Data

Feb. 25, 2013    (DE) .................. 10 2013 003 090

(51) Int. Cl.
| | |
|---|---|
| G01N 33/00 | (2006.01) |
| G01N 29/04 | (2006.01) |
| G01N 21/84 | (2006.01) |
| B31B 1/00 | (2006.01) |

(52) U.S. Cl.
CPC ................ G01N 33/00 (2013.01); B31B 1/00 (2013.01); G01N 21/84 (2013.01); G01N 29/04 (2013.01); *B31B 2201/95* (2013.01); *B31B 2203/003* (2013.01); *B31B 2203/082* (2013.01)

(58) Field of Classification Search
CPC ............... B31B 1/00; B31B 2201/95; B31B 2203/003; B31B 2203/082; G01N 33/00; G01N 21/84; G01N 29/04
USPC ........................................................... 73/584
See application file for complete search history.

(56) References Cited

U.S. PATENT DOCUMENTS

| | | | | |
|---|---|---|---|---|
| 4,177,935 A | * | 12/1979 | Centanni ................. | B31B 7/00 229/122.32 |
| 4,314,639 A | * | 2/1982 | Gloyer ............... | B65D 5/46088 206/141 |
| 4,674,332 A | * | 6/1987 | Pace ...................... | G01N 29/07 73/597 |
| 5,066,865 A | * | 11/1991 | Wennerberg ......... | G01N 21/474 250/559.01 |
| 5,342,278 A | * | 8/1994 | Kurandt ................... | B31B 1/74 493/16 |
| 5,978,499 A | | 11/1999 | Tossel | |
| 7,150,707 B2 | * | 12/2006 | Taubenheim ............. | B31B 1/00 493/125 |
| 8,073,239 B1 | | 12/2011 | Bahrami | |
| 2012/0053032 A1 | * | 3/2012 | Bruns ...................... | B31B 1/00 493/17 |

FOREIGN PATENT DOCUMENTS

| | | |
|---|---|---|
| EP | 0330495 A2 | 8/1989 |
| EP | 0557607 A1 | 9/1993 |
| EP | 0611608 A1 | 8/1994 |
| EP | 0677444 A1 | 10/1995 |
| EP | 2141487 A1 | 1/2010 |

* cited by examiner

*Primary Examiner* — J M Saint Surin
(74) *Attorney, Agent, or Firm* — Epstein Drangel LLP; Robert L. Epstein (57) ABSTRACT

In a method for testing a box blank formed from flat material, the said box blank is guided along a blade (12). At least one of the layers (10) is folded onto the blade (12), so that it is located between the layers (10, 14). A component (16) is located opposite the blade (12), which component is located outside the box blank (2). Waves (17, 21) which are affected by the layer (10) are propagated between the blade (12) and the component (16). In order to achieve a high contrast, the blade has at least one physical property which differs from the corresponding physical property of the box blank.

13 Claims, 5 Drawing Sheets

Fig. 1

METHOD AND DEVICE FOR TESTING BOX BLANKS

The present application claims priority to German Patent Application no:
DE 10 2013 003 090.0, filed Feb. 25, 2013

FIELD OF THE INVENTION

The invention relates to a method for testing at least one box blank formed from flat material and to a device for carrying out this method.

DESCRIPTION OF THE PRIOR ART

EP 2 141 487 A1 has disclosed an inspection system for detecting dirty areas on cartons. To this end, the carton is detected by using a camera.

EP 0 611 608 A1 discloses a method for the three-dimensional scanning of elevations of an object. In this case, a considerable amount of effort is expended on apparatus. In addition, the evaluation of the measured results requires a great deal of computation. Therefore, only relatively slow scanning can be carried out in this way, which is unsuitable for an industrial production process.

U.S. Pat. No. 5,978,499 A discloses a device for the inspection of cartons which detects the outer edges of the cartons by means of web edge sensors.

EP 0 330 495 A2 discloses an inspection system for packages which uses line cameras. Even using this inspection system, only the outer edges of the packages can be detected.

EP 0 677 444 A1 discloses an optical monitoring method. Here, an object is recorded by using a camera and compared with a reference. Defective objects are detected from deviations between the recorded current image and the stored reference image.

U.S. Pat. No. 8,073,239 B1 discloses a generic device. In this device, a corrugated board box blank is transported and simultaneously folded in layers over one another. The folded-together ends are bonded to one another by means of adhesive tabs. Here, it is important that the folding and subsequent bonding are carried out precisely. For this purpose, the device has a light source and a camera, which scan the box blank optically in accordance with the reflection principle. It frequently occurs that the folded and bonded box blank is shaped like a jacket. In this case, the bonded layer rests directly on the layer lying underneath. In this case, the reflection method scans both layers jointly, so that the marginal edges of the box blank, which are of interest for the quality assessment, cannot be determined with the necessary contrast. Therefore, this known method is restricted to the application of special cases and cannot be used universally. This known device and this method form the starting point of the present invention.

The invention is based on the object of devising a method and a device for carrying out this method of the type mentioned at the beginning, which can be used universally in the most diverse applications.

According to the invention, this object is achieved by the following features.

BRIEF SUMMARY OF THE INVENTION

The method according to the invention is used to test at least one box blank formed from flat material. The box blank preferably consists of cartonboard or corrugated board, in particular for producing packages. However, the method according to the invention is not restricted to these materials. The at least one box blank is transported in a running direction in order preferably to be able to produce a multiplicity of box blanks sequentially. The box blank is folded transversely with respect to the running direction in layers on one another. Consideration is in particular given to joining these layers folded on one another to one another; different connecting means such as bonding, stapling or riveting can be used for this purpose. As a result of the connecting, the box blank yields a tube-like body, which is, however, collapsed flat. The box blank itself can be printed or unprinted. It is important, for several reasons, that this folding is exact. Precise folding increases the stability when the box blank is finally folded into its geometric shape. In addition, folding machines tend to form a material blockage in the event of imprecise folding. In particular in the case of printed box blanks, exact folding is important also to achieve a clean printed image in the region of the connecting point. Here, it is in particular important that marginal edges of the box blank, running substantially perpendicular to the connecting point, are aligned with one another as accurately as possible. Otherwise, the result would be an undesired offset between the outer surfaces of the box blank and, possibly, a corresponding offset in the printed image. Making this more difficult is the fact that these marginal edges do not always run in a straight line. On the other hand, the setting of the exact overlapping length is also important in order, for example, to ensure a most exact cuboidal shape of the developed box blank and to set a correct gap width. In order to ensure this, the method according to the invention must be able to detect corresponding alignment errors reliably. However, in this connection it is problematic that the box blank is generally folded in layers on one another, that is to say is present in a flat configuration. It is therefore necessary to ensure that, in this method, marginal edges of that layer of the box blank which have been turned over during the folding operation are detected. On the other hand, the layer that is not moved during the folding operation must if possible be excluded from the testing.

In order to solve this problem, the at least one layer is folded onto at least one blade which, after the folding operation, is thus located between the layers of the at least one box blank. At least one component, which is provided outside the box blank, is located opposite this at least one blade. In this way, it is ensured that only the at least one layer which has been turned over during the folding operation and is to be tested is located between the at least one component and the at least one blade. On the other hand, the at least one layer that is not moved during the folding operation is covered by the at least one blade. Waves are propagated between the at least one blade and the at least one component, with the aid of which waves the at least one layer located between the at least one blade and the at least one component is scanned. For this purpose, the at least one blade has at least one physical property with respect to the waves which differs from the corresponding physical property of the at least one box blank. In this way, it is ensured that contrast in the wave propagation between the at least one blade and the at least one component is achieved, depending on whether or not the at least one layer of the at least one box blank is located between the at least one blade and the at least one component. In this way, the marginal edges of the at least one layer to be examined can be detected exactly, so that their mutual alignment can be tested.

For the waves used, both acoustic and electromagnetic waves have proven worthwhile. Suitable acoustic waves are in particular ultrasonic waves, since these are less sensitive to interfering noises than acoustic waves in the audible range. In the case of electromagnetic waves, the optical range from the near infrared as far as the near UV is to be preferred in particular, since in this way the result is a particularly compact structure with a simultaneously high scanning accuracy. In each case, it is important that the waves used are actually affected by the layer of flat material. If, for example, the flat material consists of fully transparent plastic, then the use of visible light is recommended unless reflective properties of the material are used. On the other hand, if the flat material is very permeable to air, then the acoustic detection of the at least one layer can become problematic. In this case, electromagnetic waves are to be preferred.

For the selection of that physical property which, with respect to the at least one blade, is different from the at least one box blank, there are various options, depending on the structure of the testing device. For example, the reflectivity with respect to the waves used could be different. In this way, waves originating from the at least one component are reflected differently from the at least one box blank, on the one hand, and from the at least one blade, on the other hand. Here, it is in principle unimportant whether this difference in the reflectivity depends on the wavelength and/or the polarization of the waves. If appropriate, the contrast achieved in this case can be improved by means of appropriate filters or appropriate polarization of the waves.

Alternatively or additionally, this physical property can also be a rotation of the polarization of the reflected light in relation to the incident light. In this case, however, it is necessary to ensure that the waves are transmitted in the direction of the at least one blade with a fixed, predefined polarization, the reflected light then being evaluated with respect to its polarization properties. It is then possible to detect which regions of the at least one blade have been covered by the at least one layer.

As a further alternative or in addition, the emission of the waves could be used as a different physical property. In this case, the at least one blade would itself generate the waves and direct them towards the at least one component. Where the at least one blade is covered by the at least one layer, the waves will be correspondingly damped until they are completely shadowed. This variant is advantageous in particular in the case of printed materials since, in this way, a high contrast can always be achieved, irrespective of the printing inks and patterns selected.

As a further alternative or in addition, the ability to detect the received waves could be used as a different physical property. In this case, the at least one blade would have to be equipped with at least one detector which receives the waves emitted by the at least one component. In this case, the waves are also damped by the at least one layer, in order to supply the necessary contrast. This method is also independent of possible printing of the flat material.

One fundamental problem of the at least one blade resides in the fact that it can be supported only in a region in which the at least one layer has not yet been folded onto the at least one blade. Only in this region is the at least one blade accessible from outside. On the other hand, the at least one blade must reach as far as into a testing area, it being possible for at least one folding unit and possibly a gluing unit to be located between the possible fixing point of the at least one blade and the testing area. Since the at least one box blank is transported onward continuously, the result is generally a still considerable blade length. In addition, the problem results that the at least one blade must not have an excessively high thickness, so as not to deform the box blank and therefore not to impair the connection either. Under these secondary conditions, the result for the at least one blade is generally a structure which is not intrinsically dimensionally stable. In order nevertheless to align the blade correctly, it is supported by the at least one layer. It is therefore ensured that the at least one blade is aligned correctly with respect to the at least one box blank, even in the end region. Alternatively, the blade can also be formed in a dimensionally stable manner, if the box blanks permit this.

In order to obtain exact data about the course of the edges to be tested, the waves are detected in a locally resolved manner. In this case, it is in principle sufficient to detect the waves in a locally resolved manner transversely with respect to the running direction of the at least one box blank. Because of the transport of the at least one box blank, local resolution can be achieved in the running direction, for example by repeated detection of the waves at appropriate time intervals. The corresponding measured data can then be converted into a two-dimensional image via the known speed of the at least one box blank. Alternatively, the waves can also be detected in a two-dimensionally locally resolved manner, which results directly in a corresponding image. Irrespective of the selection of the image acquisition method, the image obtained is then subjected to image processing. Within the context of this image processing, the image obtained can, for example, be compared with a reference image. Here, deviations from the reference image indicate corresponding alignment errors. In this case, a threshold is preferably defined, starting from which deviations are no longer tolerable. The result of the image processing in this case is a digital signal which indicates whether the box blank folded in layers on one another lies within the tolerance limits or not. As a rule, however, the image comparison is not carried out pixel by pixel, since this would lead to a very high failure rate. Instead, digitization, shifts and possible rotations are performed on the image, in order to bring the measured image into the best possible agreement with the reference image. Only after these operations are these images compared with each other. Alternatively, the exact edge positions, gap widths, gap shapes or the like can also be determined directly from the image obtained by using known image processing operations. For instance, this is done by calculating the gradient of the image and by subsequent threshold value filtering. In this case, it may be possible to dispense with a reference image and instead for the actual alignment of the edges on one another to be tested and/or for the shape of gaps to be measured directly.

To carry out the method, a device having the following features has proven worthwhile. The device according to the invention is used for testing at least one box blank formed from flat material. The said box blank is transported in a running direction and is folded transversely thereto in layers. The device has at least one emitter and at least one detector for waves, consideration being given in particular to acoustic and/or electromagnetic waves. It is important that these waves are sufficiently highly affected by the at least one folded-over layer of the at least one box blank, so that a contrast that can be evaluated is produced between the at least one layer, on the one hand, and an area outside this at least one layer, on the other hand. For this purpose, the device has at least one blade, which is held between the layers of the at least one box blank. This prevents a layer of the at least one box blank that has not been folded over impairing the measuring operation. In addition, at least one component is provided, which is located outside the layers. The at least one folded-over layer of the at least one box blank, the alignment of which is to be tested, is provided between the at least one blade, on the one hand, and the at least one component, on the other hand. For this purpose, the at least one emitter and/or the at least one detector is provided in the at least one blade and/or in the at least one component. Here, the at least one emitter and the at least one detector can be provided jointly in the at least one component or in the at least one blade. Alternatively, the at least one emitter and the at least one detector can also be provided on the one hand in the at least one blade and on the other hand in the at least one component, this assignment being in principle arbitrary. It is merely important that the at least one detector is able to receive the waves from the at least one emitter following the influencing by the at least one layer of the at least one box blank. The result here is either a reflex or a fork arrangement. In order to achieve sufficient contrast through the at least one layer of the at least one box blank, the at least one blade has at least one of the following properties:

The at least one blade can contain the at least one emitter. In this case, the waves are output from the at least one blade. The at least one layer of the at least one box blank is able to damp the waves, so that appropriate contrast is achieved.

Alternatively or additionally, the at least one blade can also contain the at least one detector. In this case, the waves are picked up by the at least one blade and converted into corresponding electric signals. In this case, the at least one emitter is preferably located in the at least one component, so that a fork arrangement results. However, consideration is also given to equipping the at least one blade both with the at least one detector and with the at least one emitter. In this case, the waves are both sent out and also detected by the at least one blade, so that a reflex arrangement results. In this case, the reflection of the waves is preferably carried out by a reflector that is contained in the at least one component and reflects the waves appropriately.

Alternatively or additionally, the blade can also have a reflectivity for the waves which differs from the reflectivity of the layer of the box blank. In this case, the at least one emitter and the at least one detector are preferably accommodated in the at least one component, so that a corresponding reflection arrangement results. In this way, the result is a particularly simple structure of the at least one blade, which, for example, can be formed by a thin metal strip.

As a further alternative or in addition, the blade can also rotate the direction of polarization in order to achieve the desired contrast. In this case, the at least one emitter and the at least one detector are preferably equipped with appropriate polarization filters. All these measures permit the generation of optimal contrast in order to detect the shape of the at least one layer of the at least one box blank.

For the at least one emitter, an ultrasonic transmitter, which sends out ultrasonic waves, is suitable. In this case, the at least one detector is formed as an ultrasonic receiver. This variant is to be preferred in particular for transparent materials.

In the case of non-transparent materials, a light source is preferred as emitter and a light detector as detector. This variant is distinguished by a more compact structure and better availability of the required components.

For the light source, in particular an incandescent lamp, a gas discharge tube, a light-emitting diode or a laser has proven worthwhile. In particular in order to achieve a very flat structure of the at least one blade, preference is given to light-emitting diodes. In particular, consideration is given to light-emitting diodes made of organic material, which can be produced as flat plastic webs.

For the light detector, in particular a photodiode, a phototransistor or a camera has proven worthwhile. In the case of the camera, consideration is given in particular to line and surface cameras. The actual transmission technology of the camera plays only a subordinate role in this case. In particular, consideration is given to CCD cameras and also to CMOS cameras. However, this enumeration is not to be understood as final.

In order to be able to form the at least one blade particularly thinly, the at least one light source and/or the at least one light detector can be assigned at least one fibre, preferably a glass and/or plastic fibre. This fibre can lead the light away from the light source or to the light detector. By means of this measure, the light source and the light detector can be arranged in an area of the at least one blade in which the blade thickness plays no part. This is, for example, an area in which the at least one box blank has not yet been folded into layers on one another. The fibres then undertake the transport of the light to or from the test area.

To achieve uniform illumination of the test area, in particular in the case of point light sources, at least one diffusing screen is provided in the at least one blade. This ensures in particular the production of diffuse light, which avoids undesired specular reflection on the box blank.

In order to achieve a statement relating to the test result from the image data obtained from the detector, at least one image processing device is arranged downstream of the latter. This device generates a decision criterion from the image data relating to the extent to which the at least one box blank produced corresponds to the requirements. This decision criterion can be used to separate out or mark poorly folded box blanks or to generate an alarm signal.

BRIEF DESCRIPTION OF DRAWINGS

Other advantages and characteristics of this invention will be explained in the detailed description below with reference to the associated figures that contain several embodiments of this invention. It should however be understood, that the figure is just used to illustrate the invention and does not limit the scope of protection of the invention.

Wherein.

DETAILED DESCRIPTION OF THE INVENTION

Figure 1:
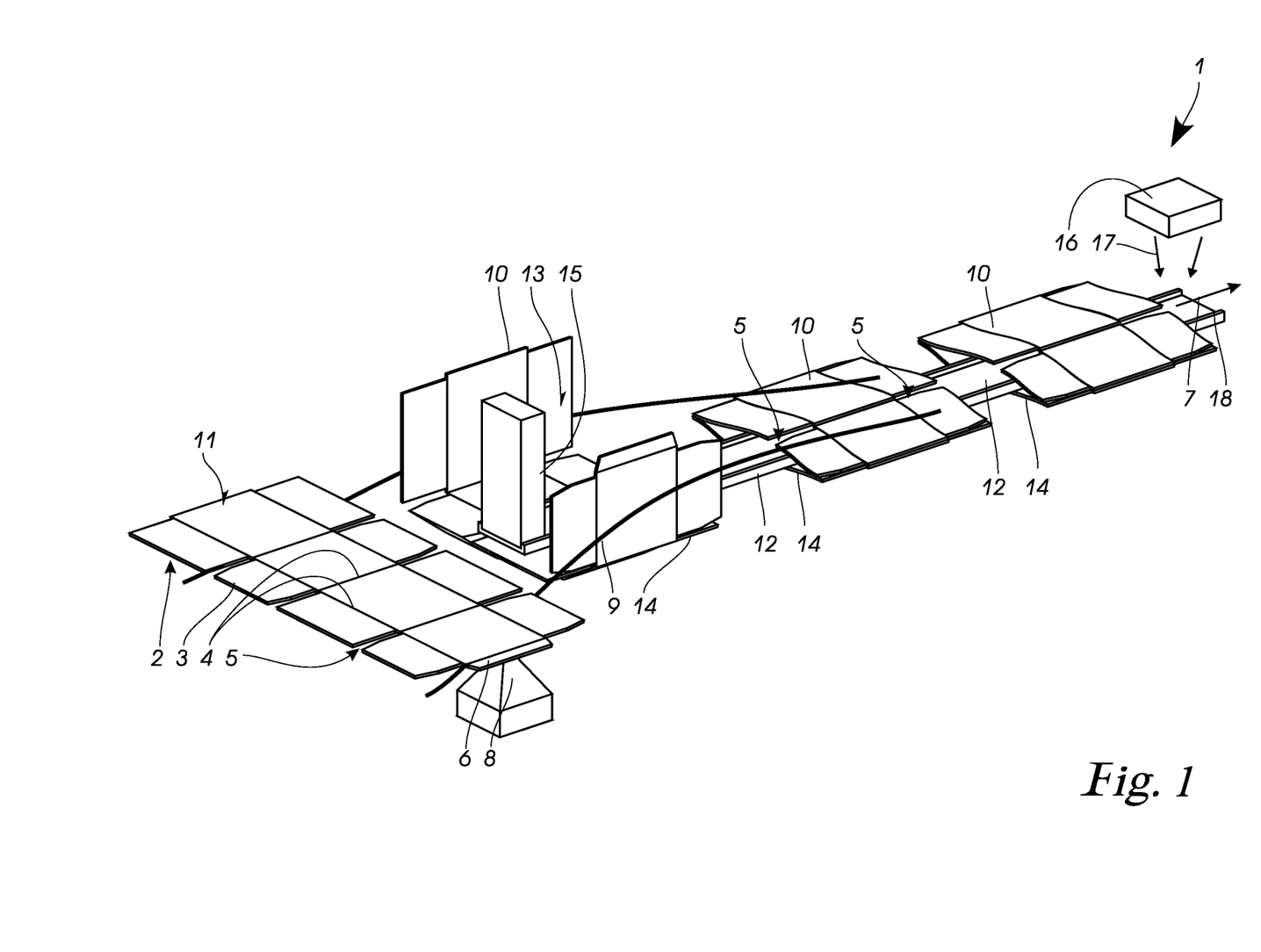
FIG. 1 shows a three-dimensional basic illustration of a device for testing at least one box blank.

FIG. 1 shows a device 1 for testing a box blank 2, consisting of a flat material 3, in particular cartonboard or corrugated board. As a rule, the box blanks 2 point downwards, so that FIG. 1 shows the device 1 from below. However, there are also installation situations in which the box blanks 2 point upwards, so that FIG. 1 shows the device 1 from above. The illustration according to FIG. 1 is a purely basic illustration, the illustration of all the components that are not important to the understanding of the subject-matter of the invention having been dispensed with.

The box blank 2 has a plurality of folded edges 4 which, for example, have been moulded into the flat material 3 by creasing or compression. In addition, gaps 5 which permit the box blank 2 to be folded together to form a cuboidal package without hindrance have been shaped out of the box blank 2. These gaps are ideally dimensioned such that bottom and top flaps just still have space in the interior of the box blank 2 assembled in a cuboidal shape. In this way, it is firstly ensured that the box blank 2 can be folded in a cuboidal shape; secondly the bottom and the top flaps stabilize the side walls of the box blank 2 and in this way ensure a considerable increase in the stability. The dimensioning of these gaps 5 results for the major part from the punch shape selected.

The box blank 2 additionally has an adhesive tab 6, in order to be able to reshape the box blank 2 to form a jacket-like configuration. Those gaps 5 which are located in the area of the adhesive tab 6 are therefore no longer defined in their shape and width solely by the punch tool but also by the folding and bonding. The greater the overlap in the adhesive area, the more narrowly will be formed the gap 5 in this area. In addition, in the event of not exactly parallel folding, angular distortions of the gap 5 result.

The box blank 2 is transported continuously in the running direction 7, the individual box blanks 2 following sequentially after one another. Indicated in FIG. 1 is a gluing unit 8, which coats the adhesive tab 6 with an appropriate adhesive. Arranged after this gluing unit is a folding unit 9, which folds over one layer 10 of the box blank 2. In the process, the adhesive tab 6 comes into flat contact with an end region 11 of the box blank 2 that is located opposite the former, and in this way ensures a permanent connection to each other.

In order to be able to check the correct folding of the box blank 2, at least one of the gaps 5 in the area of the adhesive tab 6 is analysed. For this purpose, the device 1 has a blade 12. This blade 12 extends substantially along the running direction 7 of the box blank 2. It is supported only in an area 13 in which the box blank 2 has not yet been folded over completely by the folding unit 9. Therefore, in the area 13, a layer 14 that is not to be folded over and a layer 10 that is to be folded over are present in an open configuration, so that here there is space for an appropriate supporting structure 15 of the blade 12.

Located opposite the blade 12 is a component 16. Waves which are used for testing the box blank 2 are propagated between the blade 12 and the component 16. This testing extends to at least one of those gaps 5 which are provided in the area of the adhesive tab 6. All the other gaps 5 are predefined in their geometry by a punch tool and are therefore fault-free, so that their analysis can be omitted.

In order to prevent the blade 12 from catching the adhesive tab 6 and therefore impairing the alignment of the layers 10, 14 with each other, the blade 12 has skids 18. These are provided on both sides of the blade 12 and guarantee that the blade 12 does not touch the adhesive tab 6.

Figure 2:
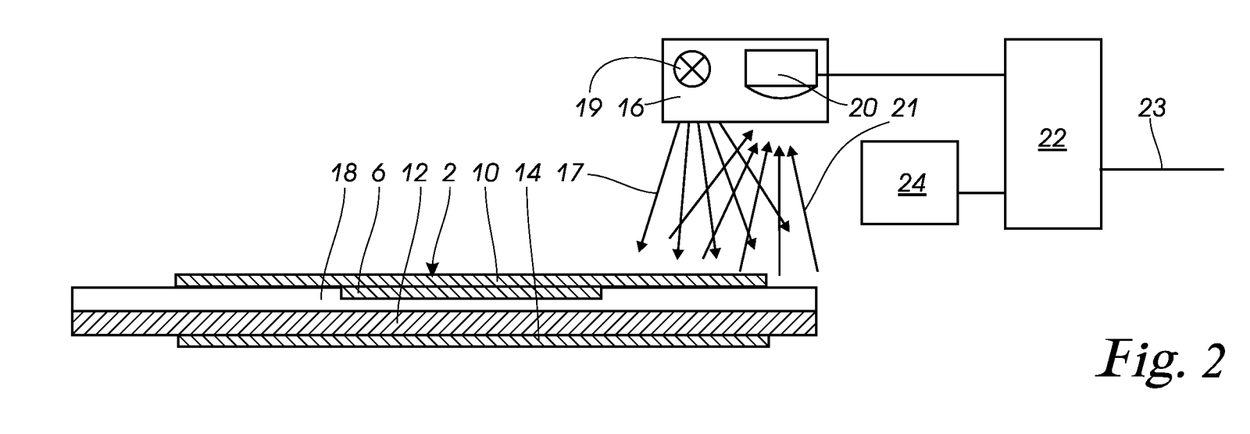
FIG. 2 shows a sectional illustration through the device according to FIG. 1.

The exact structure of the blade 12 and of the component 16 is made by using the sectional illustration according to FIG. 2. This sectional illustration reveals that the blade 12 engages between the layers 10, 14 of the box blank 2. In this way, the blade 12 prevents the gripping of the folded-over and bonded layer 10 by the layer 14 being disrupted.

An emitter 19 and a detector 20 are provided in the component 16. The emitter 19 sends out the waves 17 which, to some extent, fall onto the layer 10 of the box blank 2 and, to some extent, fall directly onto the blade 12. The blade 12 is formed in such a way that it either reflects the waves 17 well or absorbs them well. Therefore, between those areas in which the layer 10 of the box blank 2 is located and all the other areas, the result is high contrast in the reflected waves 21, which are detected in a locally resolved manner by the detector 20.

Arranged downstream of the detector 20 is an image processing device 22, which, via a signal path 23, outputs a signal which indicates whether the box blank is located within the permitted tolerance range. Here, it is in particular important to detect an offset of the layer 10 in and/or transversely with respect to the running direction 7. For this purpose, the image processing device 22 compares the image recorded by the detector 20 with a reference image 24 and, if a predefinable error threshold is exceeded, outputs an error signal on the signal path 23. This error signal can be used, for example, to mark the faulty box blank, to separate out the latter or to trigger an alarm.

Figure 3:
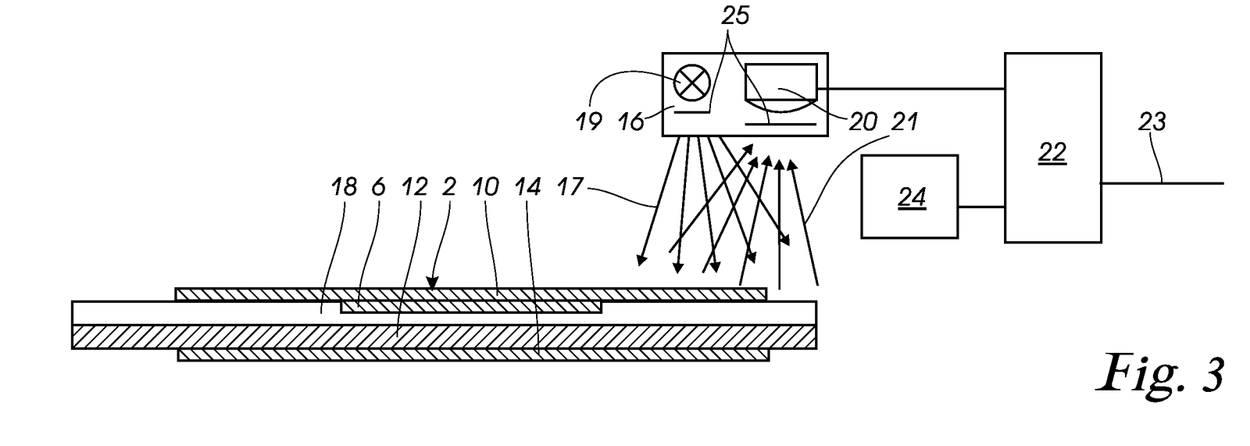
FIG. 3 shows an alternative embodiment of the device according to FIG. 2.

FIG. 3 shows an alternative embodiment, wherein the same reference symbols designate the same parts. In the following text, only the differences from the embodiment according to FIG. 2 will be discussed. In the embodiment according to FIG. 3, the blade 12 is formed in such a way that it rotates the direction of polarization of the waves 17 during the reflection. In addition, polarization filters 25 are provided in front of the detector 20 and behind the emitter 19. In this way, the rotation of the direction of polarization by the blade 12 can be detected. The box blank 2 in this case is composed of a material 3 which does not rotate the direction of polarization of the waves 17 or rotates it in another way, so that in this way a corresponding contrast is created—induced by the polarization filters 25. This contrast permits the exact detection of the layer 10.

Figure 4:
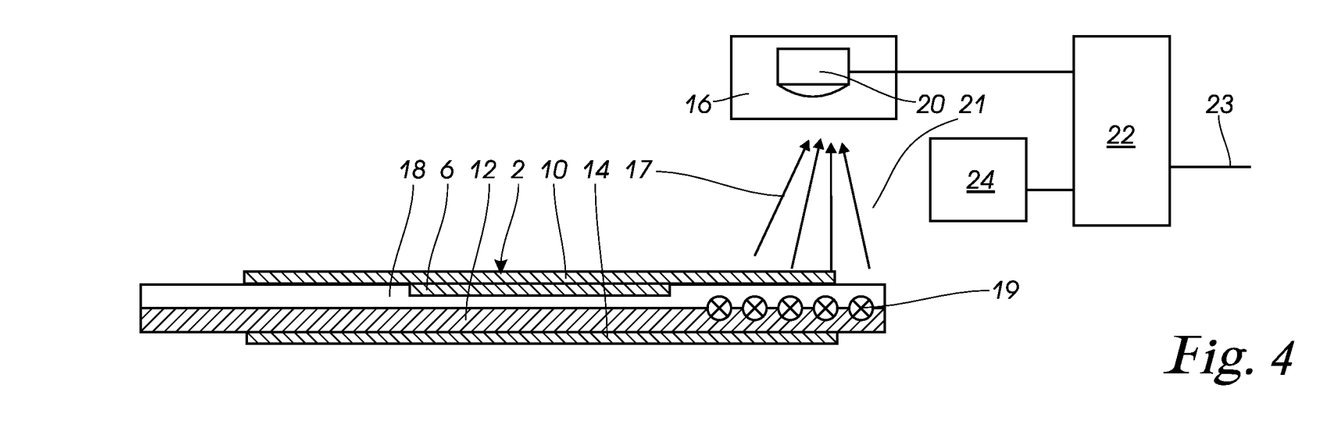
FIG. 4 shows a further alternative embodiment according to FIG. 2.

FIG. 4 shows a further alternative embodiment, in which the emitter 19 is not provided in the component 16 but in the blade 12. In this way, a fork arrangement results, the waves 17 running from the blade 12 to the component 16. Since the material 3 of the box blank 2 cannot in principle emit any waves 17, high contrast results in this way—irrespective of any possible printing of the box blank 2.

Figure 5:
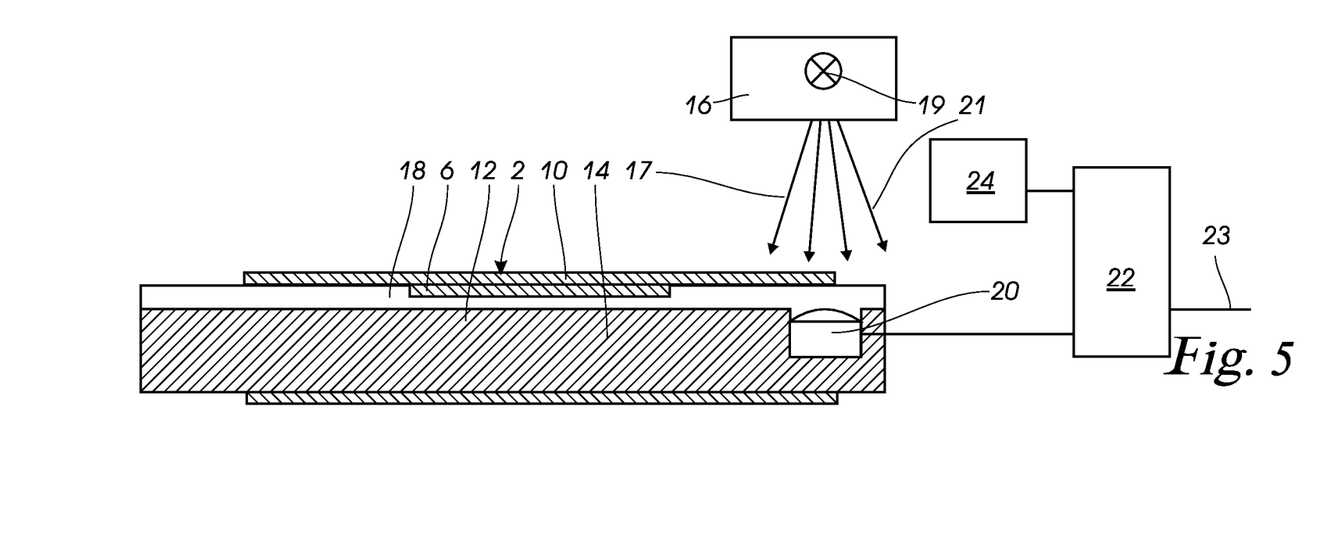
FIG. 5 shows an embodiment with a detector integrated in the blade.

FIG. 5 shows a further alternative embodiment, in which, as opposed to the embodiment according to FIG. 4, emitter 19 and detector 20 are interchanged. The detector 20 is located in the blade 12, while the emitter 19 is located in the component 16. In this case, in principle the same advantages as in the embodiment according to FIG. 4 result. However, the blade 12 generally has to be formed more thickly—necessitated by the accommodation of the detector 20. However, this generally does not play any role in the case of large box blanks.

Figure 6:
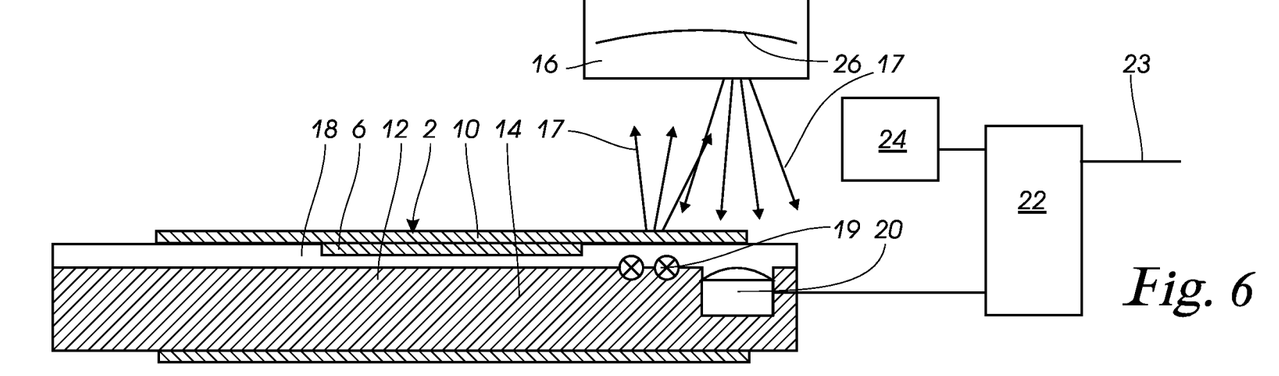
FIG. 6 shows an embodiment with a detector and an emitter integrated in the blade.

FIG. 6 shows a further alternative embodiment, in which emitter 19 and detector 20 are arranged jointly in the blade 12. In this case, a reflector 26, which reflects the waves 17 from the emitter 19 onto the detector 20, is arranged in the component 16.

Figure 7:
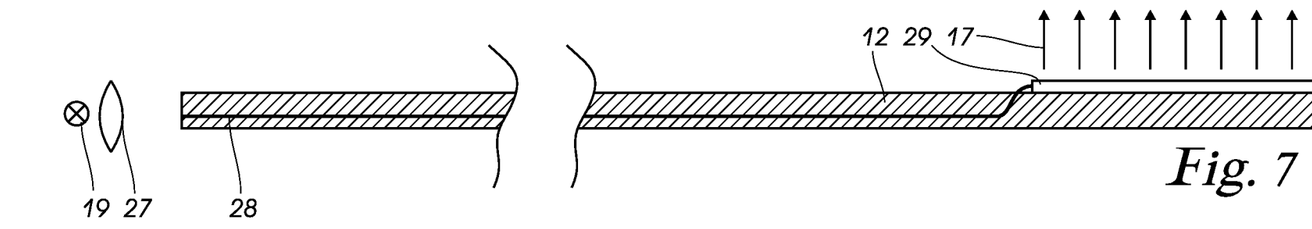
FIG. 7 shows a sectional illustration of a blade with a fibre and FIG. 8 shows an alternative embodiment of the blade according to FIG. 7 with a fibre.

FIG. 7 shows an alternative embodiment of the blade according to FIG. 4. Here, the emitter 19 is provided in the area 13 of the supporting structure 15. The waves 17 are injected into a fibre 28 by means of a lens 27. This fibre is preferably formed as a glass or plastic fibre. The fibre 28 is connected to a diffusing screen 29, which leads the waves 17 out of the blade 12. In this way, the blade 12 can be designed particularly thinly without having to accept corresponding restrictions in the formation of the emitter 19.

Figure 8:
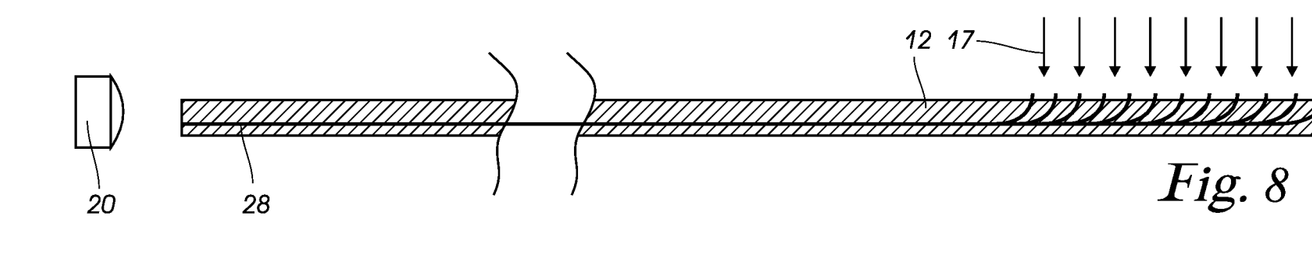

Finally, FIG. 8 shows a further alternative embodiment of the blade 12. The blade 12 contains a bundle of fibres 28, which are coupled to the detector 20. In this case, the detector 20 is provided in the area 13 of the supporting structure 15, so that its overall size does not permit the thickness of the blade 12 to become excessively large.

Figure 9:
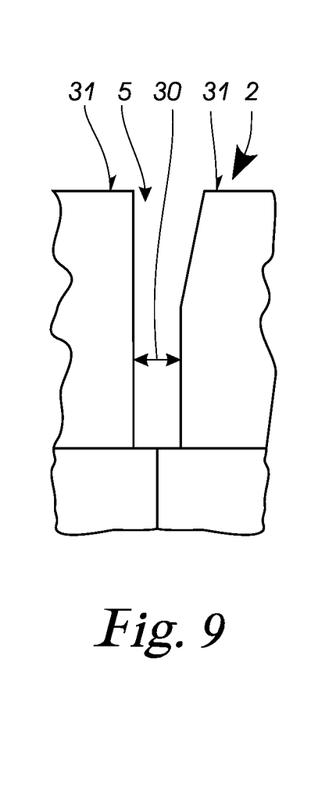
FIG. 9 shows a detailed illustration of a properly folded box blank.

FIG. 9 shows a detailed illustration of a box blank 2 with proper bonding. The gap 5 has a width 30 which corresponds to the desired value with sufficient accuracy. Front edges 31 are aligned with each other, so that the gap 5 also has the correct shape. This box blank 2 thus contains no kind of cause for complaint, and the device 1 therefore does not trigger any kind of error signal either.

Figure 10:
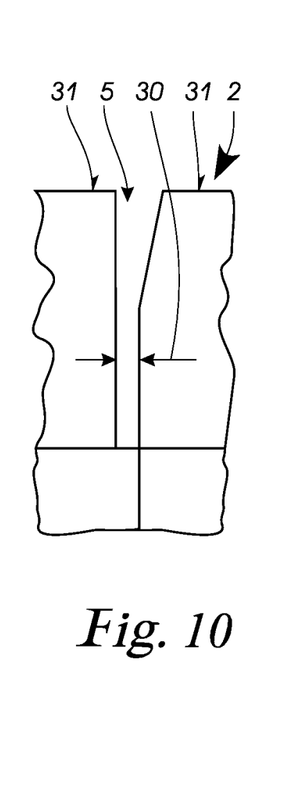
FIG. 10 shows the illustration according to FIG. 9 with too narrow a gap.

FIG. 10 shows the illustration according to FIG. 9, the gap 5 being formed too narrowly in its width 30. This is a consequence of an excessively large overlap in the area of the adhesive tab 6. This fault generally leads to the box blank 2 no longer being able to be folded into the desired cuboidal configuration, since the bottom flap strikes the side walls during the folding together. For this box blank 2, the device 1 outputs a corresponding error signal.

Figure 11:
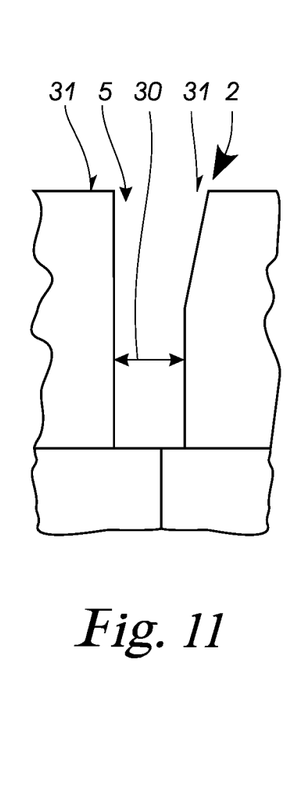
FIG. 11 shows the illustration according to FIG. 9 with too wide a gap.

FIG. 11 shows a further box blank 2 having an excessively wide gap 5. The gap width 30 therefore exceeds a specific tolerance range. A box blank 2 of this type could certainly be assembled without difficulty, but the bottom flap no longer rests on the side walls, so that it can no longer stabilize the side walls either. A box blank 2 of this type therefore does not have the necessary stability and is therefore likewise separated out by the device 1.

Figure 12:
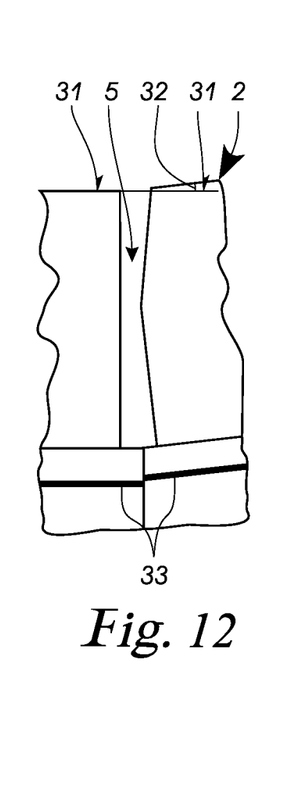
FIG. 12 shows the illustration according to FIG. 9 with an angularly distorted gap.

Finally, FIG. 12 shows a further box blank 2 in which the edges 31 are no longer aligned with each other; instead they are at an angle 32 to each other. This angle 32 is produced by an offset in the running direction 7. This fault leads firstly to problems with the assembly of the box blank 2 and secondly to an offset in a printed image 33. This offset is in particular visually not very attractive. In addition, as a result of the above-described errors, reduced stability of the box blank 2 results. The latter is accordingly likewise separated out.

Since some of the embodiments of this invention are not shown or described, it should be understood that a great number of changes and modifications of these embodiments is conceivable without departing from the rationale and scope of protection of the invention as defined by the claims.

LIST OF REFERENCE NUMBERS

1 Device 18 Skid
2 Box blank 19 Emitter
3 Material 20 Detector
4 Folded edge 21 Wave
5 Gap 22 Image processing
6 Adhesive tab device
7 Running direction 23 Signal path
8 Gluing unit 24 Reference image
9 Folding unit 25 Polarization filter
10 Layer 26 Reflector
11 End region 27 Lens
12 Blade 28 Fibre
13 Area 29 Diffusing screen
14 Layer 30 Width
15 Supporting structure 31 Front edge
16 Component 32 Angle
17 Wave 33 Printed image

The invention claimed is:

1. A method for testing at least one box blank formed from flat material, said at least one box blank being transported in a running direction and being folded transversely thereto in layers on one another by means of a folding unit, said folding unit having an area in which said blank box has not been folded over completely, said at least one box blank being guided along on at least one blade, onto which at least one of said layers is folded, so that the at least one blade is located between said layers, and at least one component comprising a detector and emitter, said component being located opposite said at least one blade, said component being situated outside said at least one box blank, wherein waves are propagated between said at least one blade and said at least one component, said at least one blade and said at least one box blank having at least one physical property with respect to said waves which differ from each other, said at least one blade being supported by at least one of said layers and said at least one blade being supported by a support structure only in said area, said waves being detected by said detector to obtain an image subjected to image processing.

2. The method according to claim 1, wherein said waves are selected from acoustic and electromagnetic waves.

3. The method according to claim 1, wherein said physical property of said at least one blade that is different with respect to the at least one box blank is selected from reflectivity, rotation of polarization, emission and ability to be detected.

4. The method according to claim 1, wherein said at least one blade is formed in a dimensionally stable manner.

5. A device for testing at least one box blank formed from flat material, said at least one box blank being transported in a running direction and being folded transversely thereto in layers by means of a folding unit, said folding unit having an area in which said blank box has not been folded over completely, said device having at least one emitter and at least one detector for waves, said device having at least one blade, said at least one blade being supported by at least one of said layers and said at least one blade being supported by a support structure only in said area, said waves being detected by said detector to obtain an image which is subjected to image processing, said blade being held between said layers, and said device having at least one component which is provided outside said layers, said at least one emitter and said at least one detector for said waves being provided in said at least one component, such that said at least one detector may receive said waves from said at least one emitter, affected by said at least one layer of said at least one box blank.

6. The device according to claim 5, wherein said at least one emitter is an ultrasonic transmitter and said at least one detector is an ultrasonic receiver.

7. The device according to claim 5, wherein said at least one emitter is a light source and said at least one detector is a light detector.

8. The device according to claim 7, wherein said light source is at least one of, an incandescent lamp, a gas discharge tube, a light-emitting diode and a laser.

9. The device according to claim 7, wherein said light detector is at least one of, a photodiode, a phototransistor and a camera.

10. The device according to claim 7, wherein said light source is assigned at least one fibre, which is able to lead light away from said light source.

11. The device according to claim 7, wherein said light detector is assigned at least one fibre, which is able to lead light to said light detector.

12. The device according to claim 7, wherein at least one diffusing screen is provided in said at least one blade.

13. The device according to claim 5, wherein at least one image processing device is arranged downstream of said at least one detector.

\* \* \* \* \*